United States Patent [19]

Lifshey

[11] Patent Number: 5,279,555
[45] Date of Patent: Jan. 18, 1994

[54] DEVICE FOR INJECTING IMPLANTS

[75] Inventor: Arthur L. Lifshey, East Brunswick, N.J.

[73] Assignee: Merck & Co., Inc., Rahway, N.J.

[21] Appl. No.: 934,831

[22] Filed: Aug. 24, 1992

[51] Int. Cl.$^5$ .......................................... A61M 31/00
[52] U.S. Cl. ........................................ 604/60; 604/57; 604/223
[58] Field of Search ................ 604/57, 59–64, 604/218, 223; 606/116, 117; 221/279

[56] References Cited

U.S. PATENT DOCUMENTS

| | | | |
|---|---|---|---|
| 3,669,104 | 6/1972 | Wyatt et al. | 604/61 |
| 4,086,914 | 5/1978 | Moore . | |
| 4,263,910 | 4/1981 | Pardekooper et al. | 604/60 |
| 4,276,878 | 7/1981 | Storz | 604/223 |
| 4,576,152 | 3/1986 | Müller . | |
| 4,657,533 | 4/1987 | Oscarsson | 604/60 |
| 4,659,326 | 4/1987 | Johnson et al. | 604/62 |
| 4,661,103 | 4/1987 | Harman | 604/62 |
| 4,673,387 | 6/1987 | Phillips et al. | 604/60 |
| 4,687,465 | 8/1987 | Prindle et al. | 604/61 |
| 4,753,636 | 6/1988 | Free | 604/49 |
| 4,769,011 | 9/1988 | Swaniger | 604/60 |
| 4,784,640 | 11/1988 | Johnson et al. | 604/62 |
| 4,799,921 | 1/1989 | Johnson et al. | 604/51 |
| 4,846,793 | 7/1989 | Leonard et al. | 604/62 |
| 4,936,827 | 6/1990 | Grimm et al. | 604/60 |
| 4,968,303 | 11/1990 | Clarke et al. | 604/218 |
| 4,994,028 | 2/1991 | Leonard et al. | 604/60 |
| 5,106,370 | 4/1992 | Stewart | 604/61 |

FOREIGN PATENT DOCUMENTS

| | | | |
|---|---|---|---|
| 223184 | 1/1959 | Australia | 604/62 |
| 272445 | 3/1965 | Australia | 604/61 |
| 831680 | 3/1960 | United Kingdom | 604/59 |

Primary Examiner—Ralph Lewis
Attorney, Agent, or Firm—Hesna J. Pfeiffer; Francis P. Bigley; Joseph F. DiPrima

[57] ABSTRACT

A device for the subcutaneous implantation of a pharmaceutical dosage form is presented. The device includes a cannula which houses the pharmaceutical dosage form and push member, all of which are prepackaged and may be sterilized. The device further includes an actuator comprising a flexible stylet, a trigger and a handle.

18 Claims, 4 Drawing Sheets

DEVICE FOR INJECTING IMPLANTS

BACKGROUND OF THE INVENTION

Subcutaneous implantation of a pharmaceutical dosage forms is recognized as a potentially advantageous approach to drug delivery. Contraceptive implants may currently be introduced subcutaneously which provide effective protection for several months. These dosage forms are rapidly gaining in popularity among the medical community since treatment problems arising from poor patient compliance are eliminated. Further, depending upon the design of the pharmaceutical dosage form, treatment may be localized to that portion of the body where greater concentrations of the pharmaceutical compound is required, or treatment may result in systemic delivery of the pharmaceutical compound throughout the patient.

Although several devices have been designed to aid in implanting pharmaceutical dosage forms, these generally require application of force directly to a plunger or they may suffer from a loss of tactile sensitivity. Those devices which provide a mechanical advantage, such as a lever, to assist in delivery of the dosage form are generally unwieldy due to their size and shape. Applicant presents herein, a device for implanting pharmaceutical dosage forms which provide for mechanical leveraging to implant a pharmaceutical dosage form while maintaining a high level of tactile sensitivity and compact, ergonomically designed size.

One method for the insertion of subcutaneous pharmaceutical dosage forms involves surgical implantation. In this procedure, an incision is made at the area where the implant is desired. The implant is placed within the area using forceps or a trocar. Since the size of the incision may be large enough to require suturing, experienced medical personal are generally required to implant the dosage form.

In an effort to avoid such surgical techniques, injection system have been developed to provide a means for implantation. In U.S. Pat. No. 4,576,152, a syringe shaped cylinder containing an injection nozzle is disclosed for the implantation of bone cement. The nozzle element has a nozzle tube of reduced cross-sectional area through which a ram passes to provide high pressure injection. The system requires direct pressure to be applied to the piston. That is, no mechanical leverage is used to assist in delivery of the pharmaceutical dosage form.

In U.S. Pat. No. 4,086,914, an implant injector is disclosed for the implantation of spaced implants using a plunger system contained within a sliding member. As pressure is applied to the sliding member, the plunger moves an implant out of a cannula and into position. Again, no mechanical advantage is achieved with this system.

U.S. Pat. No. 4,661,103 discloses a magazine type implant injector which uses a slotted barrel element which is slidably mounted to an integral magazine element and cannula. Each implant advances a previously loaded implant through the cannula for implantation. Although this device allows for direct contact between the finger of the operator and the implant, no mechanical advantage is realized.

U.S. Pat. Nos. 4,659,326, 4,784,640 and 4,799,921 disclose an injector and new process of delivering an implant to cattle, wherein a double acting trigger mechanism of the injector loads a retainer and implant into a needle and then injects the retainer and implant into the animal. The injector is effectively a gun having a plunger member which moves through a bore. The plunger rod is moved by the hand trigger which is mounted centrally in the gun. Because lateral movement of the implant and plunger rod is desired, the trigger mechanism is pivoted to a yoke element which is in turn pivoted to a slider and yoked to an intermediate location on a pin which extends across the gun housing. Although mechanical advantage is realized through the use of pivot points, tactile sense may be reduced due to the loss of contiguousness between the operator and the implant due to the use of the yokes.

A gun type injector capable of dispensing pellets from a magazine rotatably supported in the injector is disclosed in U.S. Pat. No. 4,673,387. This device utilizes an injector rod which passes through the magazine and moves a pellet to be injected. The injector rod moves along a generally linear path and is operatively associated with the trigger by means of two links which provide for lateral movement of the injector rod as the trigger is depressed. Once again, some loss of tactile sense may be lost due to the links between the trigger and the device.

U.S. Pat. Nos. 4,846,793 and 4,994,028 describe a device for subcutaneous implantation of a plurality of solid, elongated medicinal pellets. The device includes a needle-like, hollow cannula within which are located a plurality of medicinal implants. The cannula is attached to a hub which slides forward and backward within a barrel. The hub has a manually engagable knob thereon so that the hub and cannula may be moved easily with respect to the barrel. The thumb of one hand is used to actuate the device. An obturator, capable of telescoping during operation, extends from the rear of the barrel into the proximal end of the cannula. Once the cannula is inserted through the skin, it is moved backward by means of the thumb knob while the barrel is maintained in a fixed position so that the operator causes the implant to remain in place under the skin as the cannula is withdrawn from around the implant. Again, no mechanical advantage is achievable with this device.

In U.S. Pat. No. 4,753,636, a presterilized, packaged, subcutaneous contraception kit which comprises a cutter device for incising skin and a subcutaneous deposit mechanism in the shape of a tapered hollow body is presented. The device is placed within an incision and used for blunt dissecting prior to implantation of the contraceptive device. As the tool is retracted, a plunger is depressed and a contraceptive device is delivered to the site.

The present invention has improved the implantation techniques needed to deliver implantable pharmaceutical dosage forms to their desired location. This unique device provides an unexpectedly high degree of tactile sense such that the operator can more accurately position the pharmaceutical dosage form subcutaneously or within bone or other biological tissue without excessive damage to surrounding tissue. Further, this device allows for various levels of mechanical advantage to be used to deliver the pharmaceutical dosage form. Due to the unique design of the device, a safety mechanism is provided which assures that excessive pressure, which might inadvertently damage the patient, is avoided. The design further provides for a smaller size device than the above mentioned hand held units, resulting in greater control over pharmaceutical dosage form implantation.

SUMMARY OF THE INVENTION

The present invention is an injector for the implantation of an implantable pharmaceutical dosage form in animals. The device comprises (a) a housing having an internal chamber, the housing further comprising a cannula receiver means and a trigger slot communicating the outside of the housing with the internal chamber;

(b) a cannula having an internal bore throughout length of the cannula;

(c) a flexible stylet operably associated with the chamber and the cannula bore, the flexible stylet having a forward end and rearward end, the forward end movable into the cannula bore;

(d) a trigger means for moving the forward end of the flexible stylet in the housing chamber and into the cannula bore, the trigger means being pivotally the cannula bore, the trigger means being pivotally attached to the housing at the trigger pivot point, and having a first exposed end fashioned for operator manipulation and a second end which terminates within the internal chamber of the housing, the second end of the trigger means being connected and in direct contact with the rearward end of the flexible stylet;

(e) the cannula having a proximal and distal end, wherein the distal end is beveled and sharpened to provide an incising edge for easy insertion into skin, bone or animal tissue, the distal end having a connecting means suitable for attachment of the cannula to the housing, the cannula bore sized to contain a pharmaceutical dosage form and a push member, wherein the pharmaceutical dosage form resides inside the cannula and terminates near the distal end of the cannula, and the push member lies inside the cannula and near the proximal end of the cannula;

wherein, when a force is exerted on the first exposed end of the trigger means, the second end of the trigger means moves the flexible stylet through the cannula receiver of the housing, into the cannula connecting means and into the cannula where the forward end of the flexible stylet contacts and moves the push member, the push member applying a force to the dosage form such that the dosage form moves from within the cannula out into the environment of use.

BRIEF DESCRIPTION OF THE DRAWINGS

FIG. 4 (a) is a side view of the cannula assembly. FIG. 4 (b) is an exposed side view of the cannula assembly. The cannula cover and tamper evident foil seal are shown at the distal and proximal ends of the cannula. These provide a moisture and sterility seal for the push member and the pharmaceutical dosage form located within the cannula.

DETAILED DESCRIPTION OF THE INVENTION

The present invention is an injector for the implantation of an implantable pharmaceutical dosage form in animals. The device comprises (a) a housing having an internal chamber, the housing further comprising a cannula receiver means and a trigger slot communicating the outside of the housing with the internal chamber;

(b) a cannula having an internal bore throughout the length of the cannula;

(c) a flexible stylet operably associated with the chamber and the cannula bore, the flexible stylet having a forward end and rearward end, the forward end movable into the cannula bore;

(d) a trigger means for moving the forward end of the flexible stylet in the housing chamber and into the cannula bore, the trigger means being pivotally attached to the housing at the trigger pivot point, and having a first exposed end fashioned for operator manipulation and a second end which housing, the second end of the trigger means being connected and in direct contact with the rearward end of the flexible stylet;

(e) the cannula having a proximal and distal end, wherein the distal end is beveled and sharpened to provide an incising edge for easy insertion into skin, bone or animal tissue, the distal end having a connecting means suitable for attachment of the cannula to the housing, the cannula bore sized to contain a pharmaceutical dosage form and a push member, wherein the pharmaceutical dosage form resides inside the cannula and terminates near the distal end of the cannula, and the push member lies inside the cannula and near the proximal end of the cannula;

wherein, when a force is exerted on the first exposed end of the trigger means, the second end of the trigger means moves the flexible stylet through the cannula receiver of the housing, into the cannula connecting means and into the cannula where the forward end of the flexible stylet contacts and moves the push member, the push member applying a force to the dosage form such that the dosage form moves from within the cannula out into the form moves from within the cannula out into the environment of use.

Figure 1:
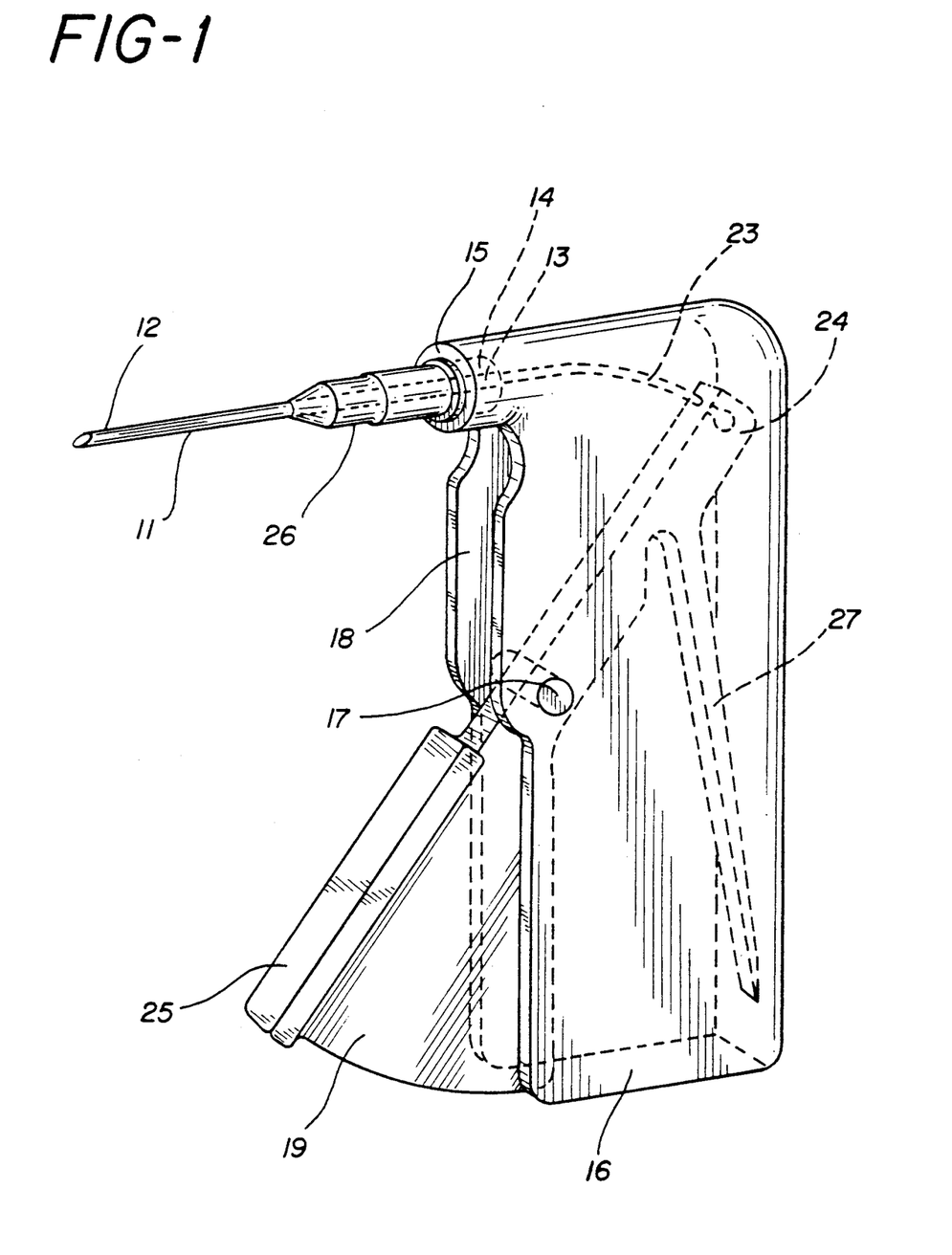
FIG. 1, is a perspective view of the device showing the cannula, cannula connecting means, housing and trigger.

Referring to FIG. 1, there is shown in perspective, a view of the present invention. The invention includes a hollow cannula (11) which has a proximal end (13) and a distal end (12). The distal end of the cannula (12) may be beveled and sharpened. The cannula (11) is typically formed of surgical steel and ranges in size from about mm to about 1.8 mm outside diameter with about 1.27 mm being the most common outside diameter. The bevel may be a "B" or "intravenous" cutting bevel of known type which allows the cannula to puncture the skin without a prior incision and without coring of flesh or body fluids. Other bevels may also be used. Although the distal end of the cannula (12) includes a bevel, it is within the scope of this invention that the injector may be used, to one skilled in the art, to implant pharmaceutical dosage forms through an existing incision made by other means. The proximal end of the cannula (13) is contained within a molded plastic hub (26) which has a connecting means (14) which allows for attachment and detachment of the cannula to the housing cannula receiver means (15).

The housing unit (16) is hollow and may have a variety of shapes. The housing unit (16) may be made of an suitable material but is typically formed of plastic by means of injection molding or other suitable process. A housing trigger slot (18) is present in the housing unit (16) to allow for installation and operation of a trigger means (19). The trigger means (19) may be pivotally attached to the housing unit (16) using a pivot pin (17) as shown. In the preferred embodiment of the device, the pivot pin (17) is molded into the trigger means (19) and snaps into position within the housing unit (16). The housing unit (16) contains a cannula receiver means (15) which allows for attachment and detachment of the cannula hub (26) which contains the cannula (11).

Figure 2:
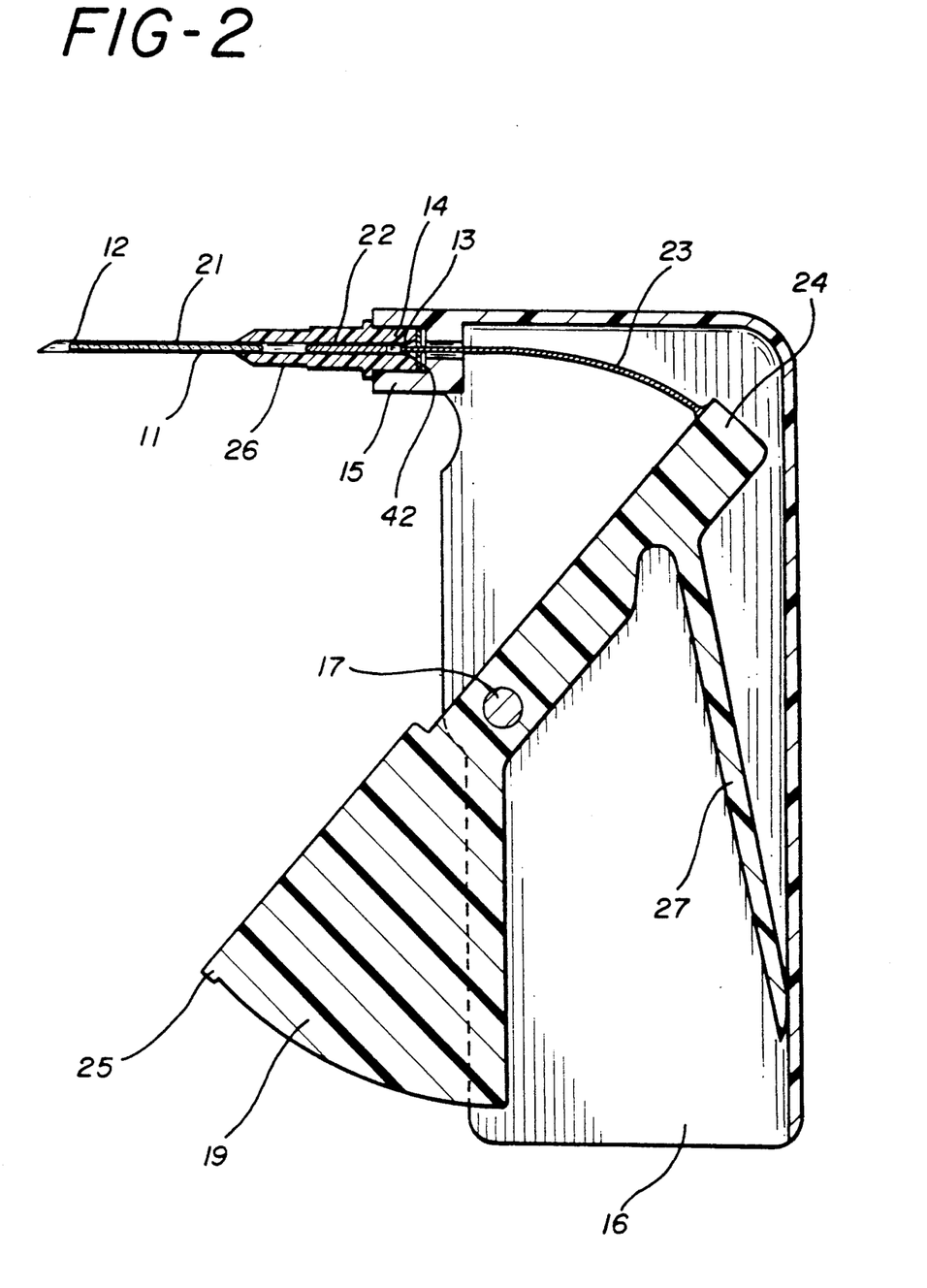
FIG. 2 is a cross sectional view of the device showing the pharmaceutical dosage form and push member located within the cannula and the flexible stylet connected to the trigger inside the housing.
Figure 3:
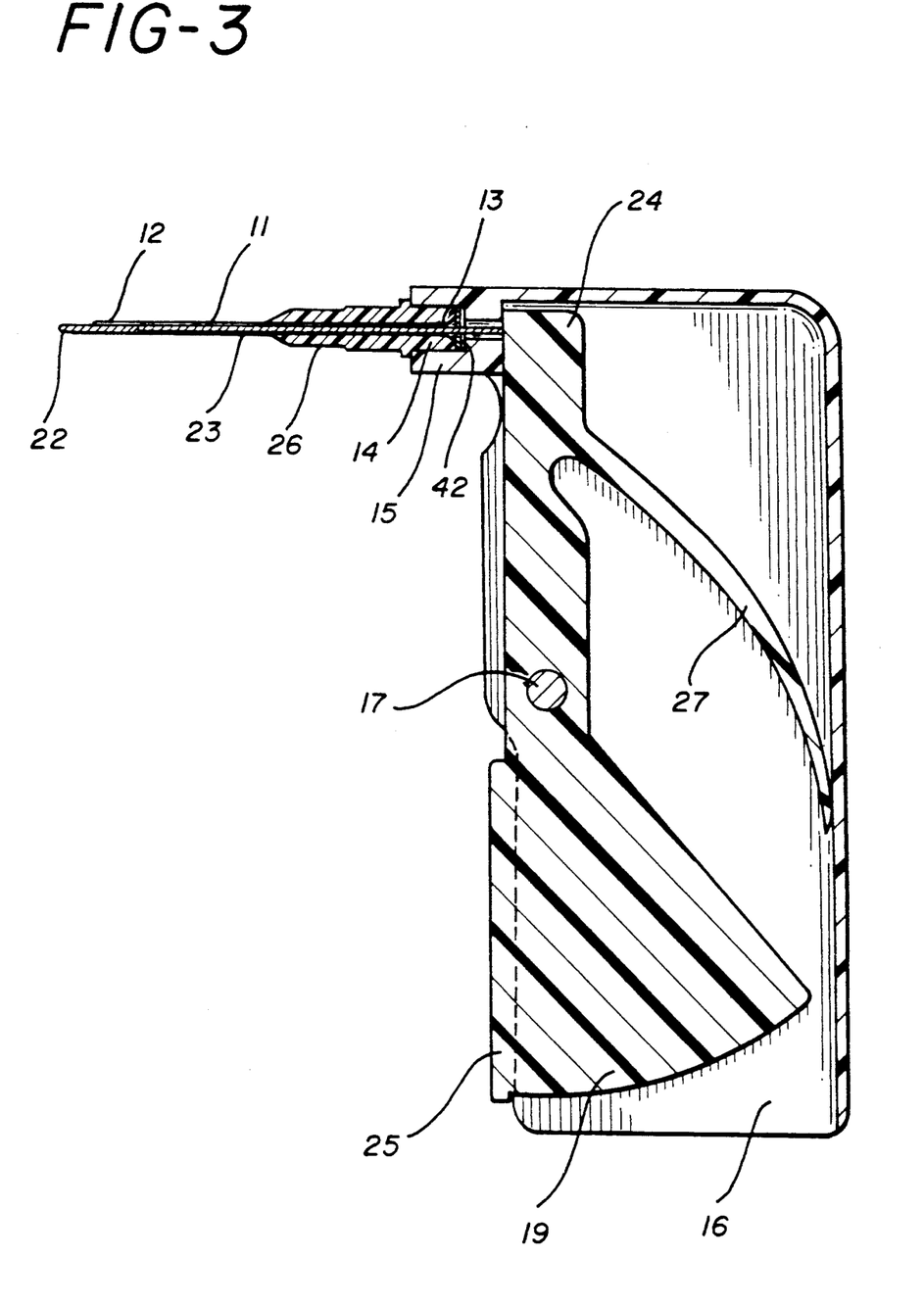
FIG. 3 is a cross sectional view of the device wherein the trigger is actuated and the flexible stylet partially extends through the cannula.

FIG. 2 shows a cross section view of one of the preferred embodiments. Here, the cannula (11) contains a pharmaceutical dosage form (21) at the distal end of the cannula (12) and a push member (22) at the proximal end of the cannula (13). A flexible stylet (23) is positioned such that the forward end abuts the push member (22) and the rearward end of the flexible stylet is fixedly inserted within, or molded as part of the second end of the trigger means (24).

Pharmaceutical dosage form (21) can be of any composition suitable for insertion delivery. For example, pellets, microcapsules, ointments, gels, thermosetting polymers containing pharmaceutically active ingredients, biodegradable polymer dosage forms, and other dosage forms known to those in the pharmaceutical sciences to be suitable for delivery in this manner, may be stored in or loaded into cannula (11) and delivered with this device.

In one preferred embodiment, a pharmaceutical dosage form which comprises a beneficial agent covalently incorporated into the backbone of a hydrolytically labile ortho ester or acetal bond is injected using this device. The pharmaceutical dosage form of this embodiment is prepared by condensing a beneficial agent such as a drug having a hydroxyl functionality of at least two and, if desired, other polyols, with diketene acetals or divinyl ethers, such that the resulting bioerodible polymeric dosage form comprises either a poly (ortho ester) or a polyacetal, wherein a statistically significant portion of the amount of monomeric beneficial agent is covalently incorporated into the resultant bioerodible polymer chain backbone. In this embodiment, shown in FIG. 4(a) and 4(b), a cannula (11), cannula cover (41), push member (22) and tamper evident foil seal (42) are sterilized before assembly. A sterile pharmaceutical dosage form (21) is then inserted into the cannula (11) and the other components are assembled and packaged under sterile conditions. The sterilized cannula assembly can therefore be provided as a separate unit to be connected to the cannula receiver of the housing, once implantation is to occur.

Figure 4A:
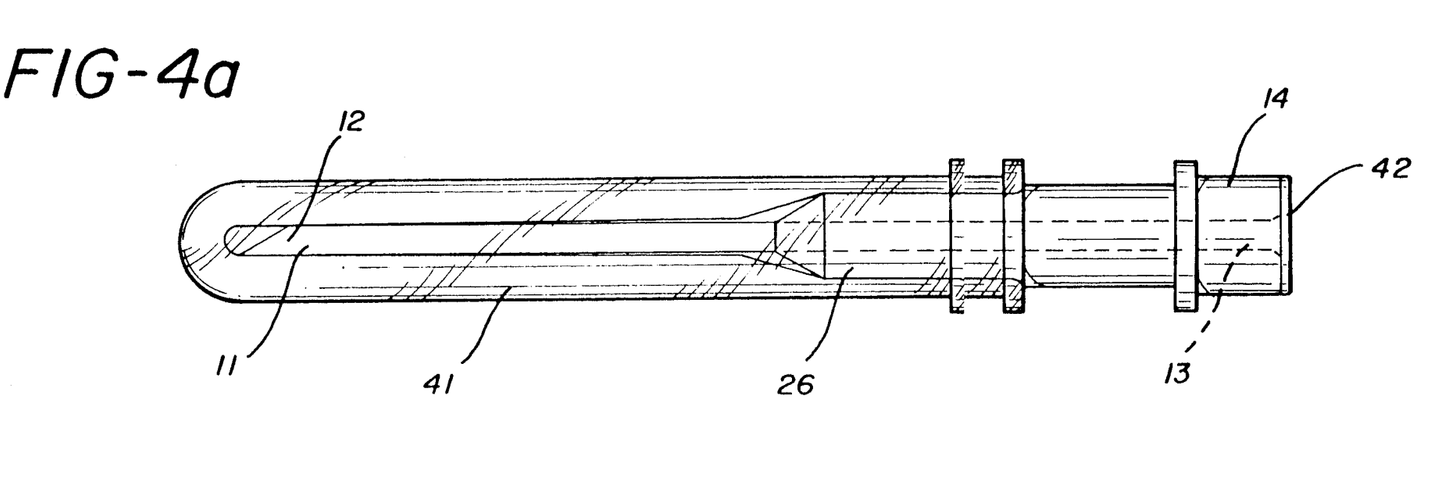
Figure 4B:
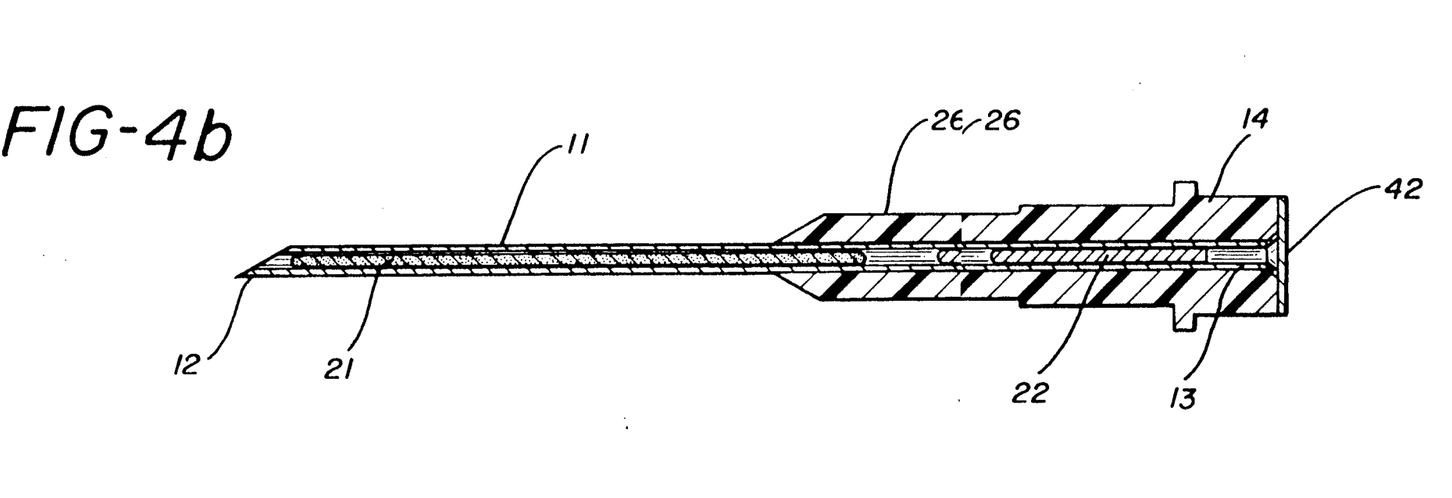

The cannula cover (41) consists of a plastic or rubber sleeve which is open at one end. The cover fits tightly over the distal end of the cannula (12) and creates a seal by pressing against the outside of the cannula (11). The cannula cover (41) forms a moisture and sterility seal by means of a tight, interference fit with the cannula hub (26). The cannula cover (41) is designed to provide both a moisture and sterility barrier for the distal end of the cannula (12).

By interference fit is meant, that the inside diameter of the opening of the cannula cover (41) is slightly smaller than outside diameter of the cannula hub (26) prior to assembly. During assembly, the cannula cover (41) expands slightly to allow a tight fit.

A tamper evident foil seal (42) is applied to the proximal end of the cannula hub (26). This foil seal (42) is composed of a polymer coated foil which can be applied to the proximal end of the cannula hub (26) using heat, ultrasonics, adhesives or other means known to those in the plastics, mechanical or pharmaceutical arts. Once applied, the foil seal (42) acts as a moisture and sterility barrier for the proximal end of the cannula (13). In one preferred embodiment, the foil seal (42) is designed to rupture when the cannula hub (26) containing the cannula (11) is attached to the cannula receiver of the housing (15). The rupture is caused by the forward end of the flexible stylet (23) piercing the foil seal (42).

The cannula hub (26) is made of plastic and is designed to be held during attachment of the cannula (11) to the housing cannula receiver means (15). The cannula hub (26) may be tapered to receive the cannula cover (41).

The flexible stylet (23) may be made of any material which is flexible and which retains its translational strength until a predetermined force is reached. Once this excess force is applied, the flexible stylet (23) is designed to buckle or break. Typical materials which have these properties are solid wire comprising stainless steel, brass, bronze and other metals. Also solid metal wire covered with plastics such as nylon, polyethylene or other plastics or covered with wound metal wire over-wrap can exhibit these properties. Additionally, braided or twisted wire cable with or without a plastic outer layer o tightly wound metal wire coil spring and molded or extruded plastics can demonstrate these properties. In one preferred embodiment, steel music wire was shown to be satisfactory. In an other preferred embodiment, the flexible stylet (23) is molded as part of the trigger means (19). The above list of materials is not meant to be inclusive. Those skilled in the mechanical art would recognize many other materials which would perform this function and which are included within this invention.

The flexible stylet (23) actually functions in the same manner as a slender column. That is, when a force is initially applied to the rearward end of the flexible stylet (23) by the trigger means (19), the forward end of the stylet will move and apply a force to the push member (22). As the force is increased, the flexible stylet (23) will continue to communicate this force to the push member (22) until a maximum force is realized. If the allowed force is exceeded, the flexible stylet (23) will buckle under the compressive load and the trigger will immediately move toward a fully actuated position, i.e. nearly open or closed depending upon the configuration of the trigger. That is, once the flexible stylet (23) has reached the point of elastic instability, the flexible stylet (23) will buckle and become ineffective in applying a force to the push member (22).

The maximum force which may be applied to the flexible stylet (23) is a function of its composition and design. Table 1 contains a listing of compressive loads and demonstrates how the composition and diameter of the flexible stylet (23) may be chosen to provide maximum force protection when using the device.

Table 1. Compressive Load Values in Pounds for Various Flexible Stylets.

| Stylet Construction | Approximate Maximum Force (P) at L = 1" |
|---|---|
| 0.040" dia. Plastic | 0.5 lbs. |

-continued

| Stylet Construction | Approximate Maximum Force (P) at L = 1" |
|---|---|
| 0.040" dia. Glass-Reinf Plastic | 1.5 lbs. |
| 0.020" dia. Stainless Steel | 3.5 lbs. |
| 0.030" dia. Stainless Steel | 17 lbs. |
| 0.040" dia. Stainless Steel | 50 lbs. |

As the approximation in Table 1 suggest, the composition and diameter of the flexible stylet (23) may be chosen to suit a specific application. That is, almost any practical buckling force can be designed into the flexible stylet by controlling diameter, materials and construction.

Where delicate subcutaneous insertion of a pharmaceutical dosage form (21) is desired, a flexible stylet (23) having a range of compressive load values from about 0.5 lbs to about 4 lbs may be desirable. When insertion of a pharmaceutical dosage form (21) into muscle tissue is required, a flexible stylet having a compressive load range of from about 2 lbs. to about 8 lbs. may be utilized. In the event the pharmaceutical dosage form (21) is to be injected into bone, cartilage or other hard material, a compressive load range of from about 10 lbs. to about 30 lbs or more may be used. These ranges are provided as a guide. However, as previously stated, the actual elastic instability of the flexible stylet will vary according to the application, and compressive load values outside these suggested ranges may be desired for a particular application.

This invention includes the use of all manner of flexible stylets (23) including but not limited to those where the diameter is relatively uniform from end to end and those where only a small portion of the column is narrowed or made of a material which will buckle under a compressive load. Further, the flexible stylet (23) may be in the form of a cylinder, or have a flat face or faces on the surface. The flexible stylet (23) may be hollow or solid.

By "buckle" is meant that the flexible stylet (23) will bend, warp or crumple under a load so as to produce a bend, bulge or other distortion in the flexible stylet once the maximum force is achieved. Fracture or breaking of the flexible stylet (23) is also contemplated by this invention, as this serves the same purpose of avoiding too great a force being delivered to the dosage form.

The flexible stylet (23) is connected directly to the second end of the trigger means (24) and comes in direct contact with the push member (22). Since the push member (22) is in direct contact with the pharmaceutical dosage form (21) tactile sensations which are delivered through the pharmaceutical dosage form (21) may also be felt at the first exposed end of the trigger means (25). As a result, obstructions which the pharmaceutical dosage form meets may be detected by the operator. An experienced operator, such as a physician or nurse, may choose to apply additional force to overcome the obstruction. However, as described previously, once a maximum force has been reached, the flexible stylet (23) will buckle alerting the operator to the fact that too much force has been applied.

The flexible stylet (23) may also be resilient. That is, after buckling, the flexible stylet (23) may regain its original shape and strength once the trigger is returned to its reset position. As a result, after applying too great a force to the first exposed end of the trigger means (25), the operator may reset the trigger means (19) by releasing the force on the first, exposed end of the trigger means (25), adjust the position of the distal end of the cannula (12) and again attempt to implant the pharmaceutical dosage form (21).

Since the flexible stylet (23) may traverse an arc, the total throw or travel of the flexible stylet (23) through the cannula (11) may exceed the linear storage space provided in the housing unit (16). That is, the flexible stylet (23) does not require as large a storage area as would a non-flexible stylet, since prior to entry into the cannula (11), the flexible stylet (23) generally remains in a curved position. As a result, the housing unit (16) can be sized to fit comfortably in one hand of an operator.

The maximum length of throw or travel of the forward end of the flexible stylet (23) ranges from about 1 cm to about 6 cm with about 4 cm being commonly specified. Although the flexible stylet (23) has the capacity to travel a set distance, pharmaceutical dosage forms of various lengths may be accommodated by positioning the push member directly behind the solid dosage form. In the case of a shorter length pharmaceutical dosage form (21), the flexible stylet (23) will have free travel until the push member (22) makes contact with the pharmaceutical dosage form (21). The flexible stylet (23) and push member (22) therefore come to rest in the same position after delivery of the pharmaceutical dosage form (21).

The push member (22) is designed to make direct contact with the pharmaceutical dosage form (21) during storage and delivery. The push member (22) is generally made of plastic, however its composition may be chosen from any of a number of materials such as polyethylene, high density polyethylene, polypropylene elastomer, stainless steel and other materials which would be well known to those skilled in the mechanical or pharmaceutical arts. Other plastics, rubber compositions or metals which are compatible with the pharmaceutical dosage form (21), which may be sterilized, and which function as a means of expelling the pharmaceutical dosage form (21) are also included within this list.

The push member (22) ranges in length from about 0.2 inches to about 1.0 inch and may be constructed as a cylinder which conforms to the internal bore of the cannula. However, other geometric patterns would also be within the scope of this invention. For example, in one preferred embodiment, the push member (22) is constructed such that the end which contacts the flexible stylet (23) is flared. This design results in a tighter seal between the push member (22) and the walls of the cannula (11) and alleviates the potential for the push member (22) to fall out of the proximal end of the cannula (13) once the tamper evident foil seal (42) is removed or ruptured. The design may further provide a moisture seal or sterility barrier to protect the dosage form.

When the push member (22) is composed of a malleable material such as polyethylene the push member (22) may be designed to remain trapped within the cannula (11) making further use of the cannula (11) difficult. This is accomplished by molding features into the push member (22) which cause it to remain lodged in the distal end of the cannula (12) once the pharmaceutical dosage form (21) has been delivered. These features may consist of, for example, a flexible protrusion which expands to halt rearward motion of the push member (22) within the cannula (11).

The push member (22), which contacts the pharmaceutical dosage form (21), may extend beyond the distal end of the cannula (12) after completely expelling the pharmaceutical dosage form (21). In such a situation, complete expulsion of the pharmaceutical dosage form (21) is assured. If the push member (22) lodges in the distal end of the cannula (12), the dangers associated with the sharpened distal end of the cannula (12) due to inadvertent pricking or scratching may be mitigated.

The cannula connecting means (14) may be any pressure fit, friction fit, taper lock, interference fit, or screw type fitting which will allow for the attachment and removal of the cannula to the housing. The housing cannula receiver means (15) is a receptor for the cannula connecting means (14). The housing cannula receiver means (15) may be molded into the housing unit (16) or it may be attached to the housing, through the use of adhesives or mechanical means prior to use.

The trigger means (19) may simply be a piece of metal or plastic which extends outside the housing unit (16), through the housing trigger slot (18) and into the chamber of the housing unit (16). The first, exposed end of the trigger means (25), that portion which extends outside the housing, may have a flat exterior or may be molded to better conform to the operators finger or thumb.

The second end of the trigger means (24) is connected directly to the rearward end of the flexible stylet. This may be accomplished by boring a hole in the second end of the trigger means (24) and inserting the second end of the flexible stylet (23) into the hole. The flexible stylet (23) may be secured within the hole of the second end of the trigger means (24), using an adhesive, by pressure fitting the two pieces, through the use of a biasing device such as a set screw or by any other means known to those in the mechanical engineering art.

Further, the rearward end of the flexible stylet (23) may be affixed to any portion of the second end of the trigger means (24) using any fastener. However, the flexible stylet (23) must be directly connected to the second end of the trigger means (24) in order to provide the most sensitive tactile information possible during the insertion process.

In one preferred embodiment, the flexible stylet (23) is molded as part of the trigger means (19). In this embodiment, a leaf spring (27) may be molded into the trigger means (19) as well. An example of this unitary construction is shown in FIG. 2.

The trigger means (19) may be positioned in any location of the housing unit (16) which provides for actuation of the flexible stylet. The trigger means (19) extends through the housing trigger slot (18) of the housing unit (16).

The trigger means (19) has two maximum position, relaxed and actuated. In the relaxed trigger position, the flexible stylet (23) is in its most contracted position relative to the cannula (11) and push member (22). In the actuated trigger position, the flexible stylet (23) is in its most extended form, relative to the cannula (11) and push member (22).

The trigger means (19) may be constructed such that reducing the distance between the first, exposed end of the trigger means (25) and the housing unit (16) results in movement of the flexible stylet (23) into the cannula (11) as shown in FIG. 1. Alternatively, the trigger may be constructed so that movement of the first, exposed end of the trigger means (25) away from the housing unit (16) result in movement of the first end of the flexible stylet (23) into the cannula (11).

The trigger may be biased in its relaxed position using any biasing means available. For example, a simple spring may be used to bias the trigger. In FIG. 2, the biasing means is molded into the trigger means (19), in the form of a leaf spring (27). Any alternative type of biasing means may be employed, including the use of a torsional spring on a pivot pin. This list is not dispositive of all biasing means which could be utilized in this device. Other biasing means are within the scope of this invention.

What is claimed is:

1. An injector for the implantation of pharmaceutical dosage forms in animals which comprises:
    (a) a housing unit having an internal chamber, the housing unit further comprising a cannula receiver means and a trigger slot communicating the outside of the housing unit with the internal chamber;
    (b) a cannula having an internal bore throughout the length of the cannula, the cannula containing a push member;
    (c) a flexible stylet operably associated with the chamber and the cannula bore, the flexible stylet having a forward end and rearward end, the forward end movable into the cannula bore;
    (d) a trigger means for moving the forward end of the flexible stylet in the housing unit chamber and into the cannula bore, the trigger means being pivotally attached to the housing unit at the trigger pivot point, the trigger means extending from outside the housing through the trigger slot and into the internal chamber, the trigger means having a first exposed end outside the housing which is fashioned for operator manipulation and a second end, which terminates within the internal chamber of the housing, the second end of the trigger means being connected and in direct contact with the rearward end of the flexible stylet;
    (e) the cannula having a proximal end and distal end, wherein the distal end is beveled and sharpened to provide an incising edge for easy insertion into skin, bone or animal tissue, the proximal end having a connecting means suitable for attachment of the cannula to the housing by way of the cannula receiver means, the cannula bore sized to contain the push member which lies inside the cannula and near the proximal end of the cannula, the push member being slidably related to the cannula bore, the push member being capable of abutting and exerting pressure on a pharmaceutical dosage form placed within the distal end of the cannula;
wherein, when a force is exerted on the first exposed end of the trigger means, the second end of the trigger means moves the flexible stylet through the cannula receiver means of the housing, into the cannula connecting means and into the cannula where the forward end of the flexible stylet contacts and moves the push member, the push member applying a force to the pharmaceutical dosage form such that the dosage form moves from within the cannula out into the environment of use.

2. The injector of claim 1, wherein the cannula, containing the pharmaceutical dosage form and the push member is capable of being sterilized.

3. The injector of claim 1, wherein the cannula is formed of surgical steel and ranges in size from about 0.5 mm to about 1.8 mm in outside diameter.

4. The injector of claim 1, wherein the cannula connecting means and the cannula receiver means are connected using a screw type fitting.

5. The injector of claim 1, wherein the proximal end of the cannula is protected by a tamper evident foil seal and the distal end is protected by a cannula cover.

6. The injector of claim 5, wherein the foil seal is pierced by the action of connecting the cannula to the cannula receiver means of the housing.

7. The injector of claim 1, wherein the housing unit is made of plastic.

8. The injector of claim 1, wherein the flexible stylet is a cylinder.

9. The injector of claim 1, wherein the flexible stylet has a flat face on its surface.

10. The injector of claim 1, wherein the flexible stylet is resilient.

11. The injector of claim 1, wherein the push member ranges in length from about 0.2 inches to about 1.0 inches.

12. The injector of claim 1, wherein the push member is a cylinder.

13. The injector of claim 1, wherein the end of the push member for contacting the pharmaceutical dosage form is designed to be retained at the distal end of the cannula after the pharmaceutical dosage form is delivered.

14. The injector of claim 1, wherein the end of the push member in contact with the flexible stylet is flared and forming a seal with the wall of the cannula.

15. The injector of claim 1, wherein a trigger pivot pin is molded into the trigger means.

16. The injector of claim 1, wherein the trigger means is biased by a biasing means.

17. The injector means of claim 16, wherein the biasing means is a leaf spring molded into the trigger means.

18. The injector of claim 16, wherein the biasing means is selected from the group consisting of an extension spring, integral leaf spring, and torsional spring.

* * * * *